(12) United States Patent
Wood

(10) Patent No.: US 6,293,280 B1
(45) Date of Patent: *Sep. 25, 2001

(54) KISSING SHIELD AND METHOD OF USE THEREOF

(76) Inventor: Deloris Gray Wood, R.R. 5, Box 134, Salem, MO (US) 65560

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/466,004

(22) Filed: Dec. 17, 1999

Related U.S. Application Data

(63) Continuation of application No. 09/124,191, filed on Jul. 28, 1998, which is a continuation of application No. 08/851,871, filed on May 6, 1997, now Pat. No. 5,787,895, which is a continuation of application No. 08/451,652, filed on May 26, 1995, now Pat. No. 5,727,565.

(51) Int. Cl.$^7$ ..................................................... A61F 11/00
(52) U.S. Cl. .................................. 128/857; 128/859; 2/11
(58) Field of Search ................................... 128/846, 857, 128/859, 861, 862; 602/902; 2/11

(56) References Cited

U.S. PATENT DOCUMENTS

| D. 210,183 | 2/1968 | Ross | D86/10 |
| D. 225,910 | 1/1973 | Kurianski | D86/10 |

(List continued on next page.)

FOREIGN PATENT DOCUMENTS

| 3920996 | 5/1990 | (DE) . |
| 948667 | 2/1964 | (GB) . |
| 1061321 | 3/1967 | (GB) . |
| 2039406 | 8/1980 | (GB) . |

*Primary Examiner*—Michael A. Brown
(74) *Attorney, Agent, or Firm*—Dunlap, Codding & Rogers, P.C.

(57) ABSTRACT

A kissing shield comprised of a thin, flexible membrane and a frame or holder. The membrane is closed on three sides, a fourth side remaining open so that the membrane can be stretched over the frame or holder. The frame or holder consists of a supporting member and an elongated handle. The supporting member adapts over the bottom part of the user's face and has sufficient dimension to cover the lips and most of the cheeks and extends from under the nose to the bottom of the chin. The elongated handle extends laterally from the supporting member and is sized to be held in the hand of the user such that the hand is spaced apart from the supporting member and membrane.

In use, the membrane is placed over the frame or holder. Using the handle portion of the frame or holder, the user places the kissing shield under his nose, so that it covers his lips, cheeks and chin. The user then positions the kissing shield between his lips and the lips or cheek of the individual he plans to kiss and kisses the intended recipient of his affection.

21 Claims, 4 Drawing Sheets

U.S. PATENT DOCUMENTS

| | | |
|---|---|---|
| 566,730 | 8/1896 | McCullen . |
| 1,166,977 * | 1/1916 | Favary ................................... 2/11 |
| 1,199,529 | 9/1916 | Collman . |
| 1,365,684 | 1/1921 | Guise . |
| 1,480,780 | 1/1924 | Pauley . |
| 1,597,806 | 8/1926 | Kvare . |
| 2,123,343 | 7/1938 | Rightsell ................................ 2/21 |
| 2,149,067 | 2/1939 | Otero .................................. 128/139 |
| 2,203,562 | 6/1940 | Edwards ............................... 2/206 |
| 2,265,529 | 12/1941 | Kemp ................................. 128/139 |
| 2,804,123 | 8/1957 | Kling ................................... 155/69 |
| 3,180,639 | 4/1965 | Cotler et al. ........................... 272/1 |
| 3,428,978 | 2/1969 | Johnson .................................. 9/11 |
| 3,477,074 | 11/1969 | Bezanis .................................. 9/11 |
| 3,695,565 | 10/1972 | Hodges ................................ 248/97 |
| 3,729,847 | 5/1973 | Chandos ............................... 40/125 |
| 3,740,768 * | 6/1973 | McCosker ............................... 2/11 |
| 3,771,247 | 11/1973 | De Harak ............................. 40/152 |
| 3,772,707 | 11/1973 | Alosi et al. ............................ 2/174 |
| 3,781,994 | 1/1974 | Hesselgren ............................. 32/35 |
| 3,802,429 | 4/1974 | Bird .................................. 128/146.2 |
| 4,034,495 | 7/1977 | Lemelson .............................. 40/137 |
| 4,050,457 | 9/1977 | Davidson ......................... 128/145.5 |
| 4,084,585 | 4/1978 | Venaleck .......................... 128/146.2 |
| 4,486,975 | 12/1984 | Harreld et al. ....................... 446/220 |
| 4,498,652 | 2/1985 | Malik .................................... 248/99 |
| 4,583,946 | 4/1986 | Shanel ................................. 433/136 |
| 4,664,628 | 5/1987 | Totaro ................................. 433/136 |
| 4,781,709 | 11/1988 | Grubman ............................ 604/349 |
| 4,815,456 | 3/1989 | Rubin et al. ........................ 128/859 |
| 4,825,878 | 5/1989 | Kuntz et al. ........................ 128/857 |
| 4,837,861 | 6/1989 | Cole ........................................ 2/9 |
| 4,856,535 | 8/1989 | Forbes ................................ 128/857 |
| 4,872,465 | 10/1989 | Kuntz et al. ........................ 128/857 |
| 4,944,312 | 7/1990 | Smith .................................. 128/857 |
| 4,974,605 | 12/1990 | Esqueda .............................. 128/857 |
| 5,112,322 | 5/1992 | Hathaway ............................ 604/317 |

\* cited by examiner

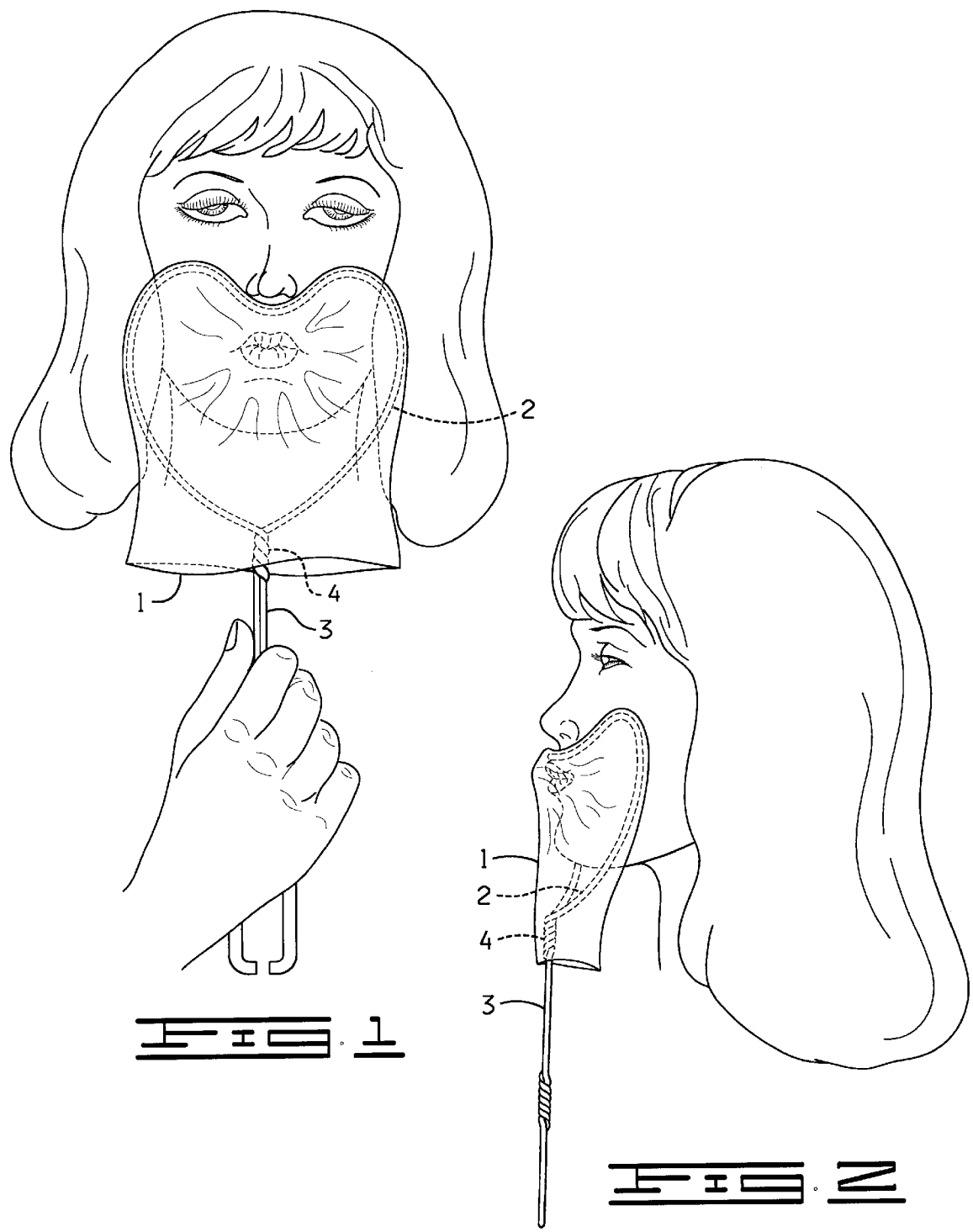

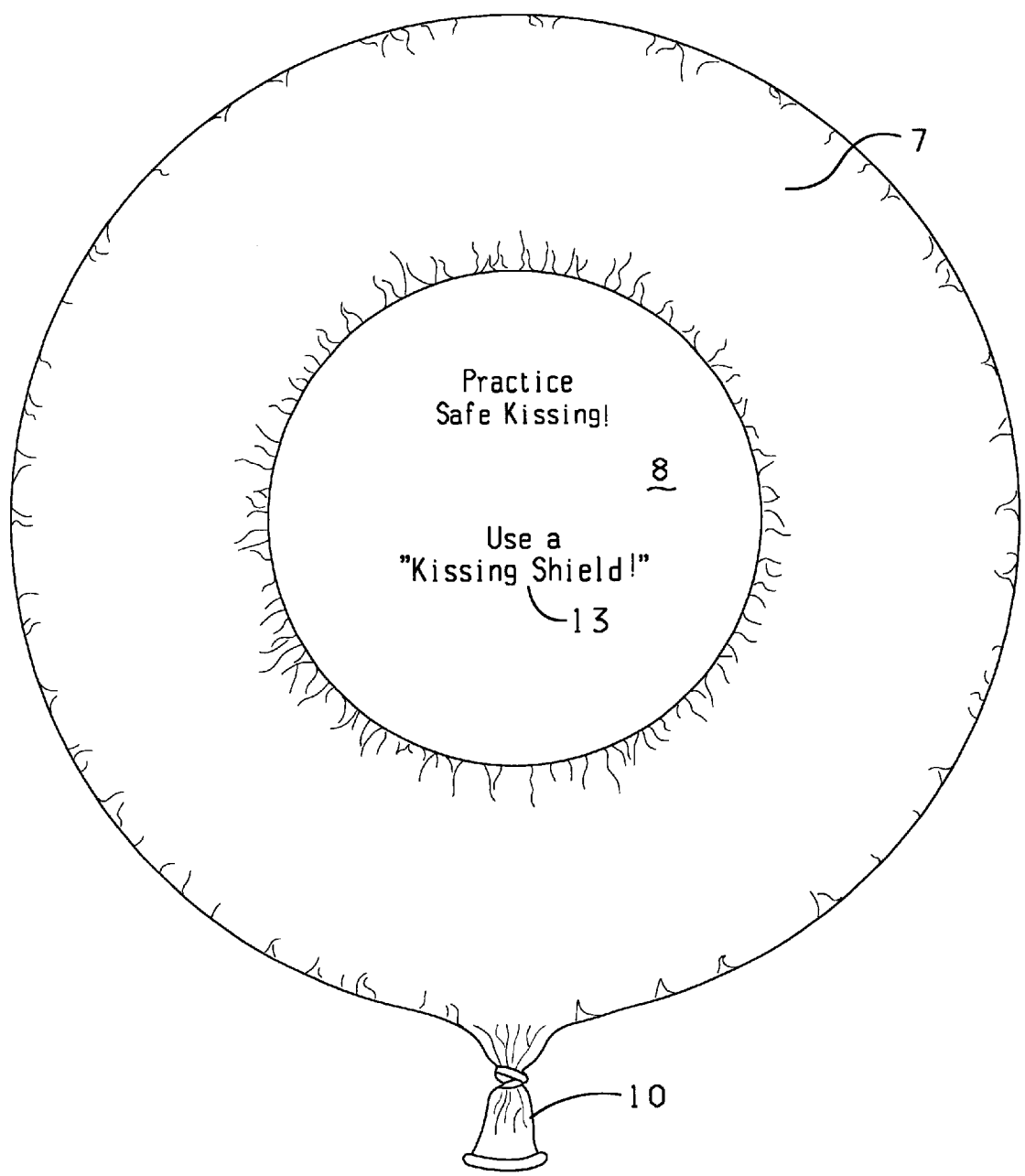

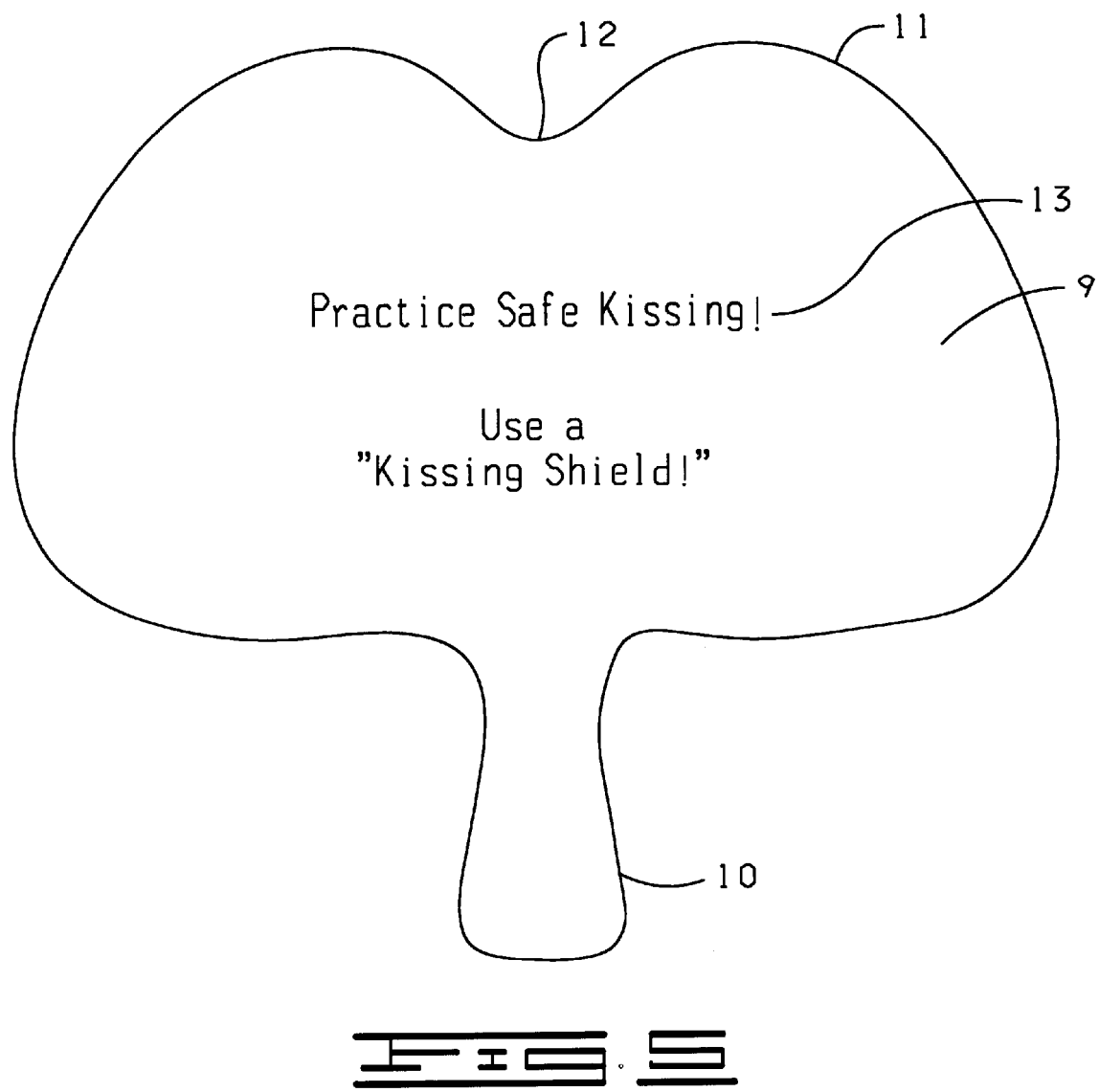

KISSING SHIELD AND METHOD OF USE THEREOF

This is a continuation of copending application Ser. No. 09/124,191 filed on Jul. 28, 1998 which is a continuation of Ser. No. 08/851,871 filed May 6, 1997 now U.S. Pat. No. 5,787,895, which is a continuation of Ser. No. 08/451,652 filed May 26, 1995 now U.S. Pat. No. 5,727,565.

The present application is a continuation-in-part application under 35 U.S.C. §120 of prior application Ser. No. 07/776,196, filed Oct. 15, 1991, which is co-pending and was a continuation-in-part of prior application Ser. No. 07/589,371, filed Sep. 28, 1990, now abandoned.

FIELD OF THE INVENTION

The present invention relates to face shields used for protection of the lips, tongue, mouth, chin, and cheeks from exposure to germs and diseases, in general, and in particular, to face shields which can be used while engaging in the act of kissing another person.

BACKGROUND OF THE INVENTION

There is a growing awareness of the seriousness of diseases, like Acquired Immunodeficiency Syndrome (AIDS), being spread and the need for protection of those not exposed to such diseases. At times, there has been hysteria among parents and other students, who are afraid their children or they themselves will become infected from classroom and playground contact, when students with AIDS or the Human Immunodeficiency Virus (HIV) have attended school. Also, persons who carry the herpes virus sometimes have lip sores which are usually not distinguishable from an ordinary canker sore or a fever blister by a lay person.

It is customary when we kiss to come in contact with another's lips, and in certain cultures, to follow with a kiss on the skin of each cheek; thus germs can be passed from one person to another. In keeping with one aspect of the invention, if casual contact is necessary and a kiss is appropriate, one can protect oneself from the germs present in saliva or other secretions which might be transmitted from kissing by using a kissing shield.

The present invention proposes a method and device in which a flexible membrane is used as a kissing shield to lessen one's chances of becoming infected by disease from casual contact. In the alternative, if a person is infected, the chances of transferring the infectious disease from one person to another could be reduced by use of a thin, resilient flexible, impervious membrane, preferably selected from the class of polyethylene, vinyl, and polypropylene materials, stretched over a frame or holder. This would lessen the spread of bodily fluids from one person to another when kissing with the end result of preventing the spread of viruses and diseases, such as canker sores, fever blisters, and AIDS, until there is a cure and prevention of the diseases. The advantages of a kissing shield over regular kissing will become apparent in consideration of the following specification and the accompanying drawings wherein there is disclosed a preferred embodiment.

The kissing shield has both social and health benefits, if basic precautions, such as those one would engage in while using a condom to practice "safe sex", or as a dentist would use when he dons rubber gloves to prevent bodily fluids, such as blood and saliva from his patient, from spreading to his hands and thereby infecting him, are used. The kissing shield can be economically mass produced so that it could be easily disposed of after kissing a person and replaces with a new one.

The kissing shield is for people who desire to be cautious when in contact with another person as they kiss. Use of the kissing shield is convenient and practical. However, like most items we use when we must alter our habits, education is an important step. The kiss is one of the first forms of affection that we display to another. It seems only natural that we would start at a fundamental level and teach "safe kissing" before we teach "safe sex".

The kissing shield, if handled properly, will help people who want to do whatever they can while kissing to practice "preventive medicine" and ensure that disease is not passed from one person to another by proper sanitation or cleanliness of one or both parties. A person who might have a disease and a person who does not want to get the disease or a person who is being protected would take precautionary moves to help prevent the spread of diseases, such as AIDS, by first practicing "safe kissing".

A kissing shield is for casual kissing. It can be used especially by a politician who kisses babies.

It is therefore a primary object of the invention to provide a simple, inexpensive kissing shield to be used when kissing mouth-to-mouth or mouth-to-cheek thereby avoiding the necessity for skin contact with the person to whom affection is intended. It is another object of the invention to provide a means for removing the hesitancy a user may have in kissing another individual without sacrificing the effectiveness of the kiss. It is a further object of the invention to provide a means of preventing the transmission of germs or viruses from saliva or other secretions and the transfer of lipstick or other cosmetics when individuals are engaged in kissing. It is another object of the invention to provide a shield which does not need to be worn. It is a final object of the invention to provide a shield which is economical in construction, such that the device can be used once and thereafter disposed of. Other objects and features will be in part apparent and in part pointed out hereinafter.

SUMMARY OF THE INVENTION

The present invention consists of a shield, which is formed of a thin, flexible, impervious membrane, and a frame or holder. In one embodiment, the membrane consists of two plies closed on three sides and open on the fourth side so as to create a bag which can be stretched over a frame or holder. The kissing shield frame or holder adapts over the bottom part of the user's face and has a handle which extends laterally from the shield and is sized to be held by the user. It has sufficient dimension to cover the lips and most of the cheeks and extends from under the nose to the bottom of the chin. The shield compresses when two sets of lips meet in a kiss or when one set of lips meets the cheek. When compresses, the thin membrane facilitates the tactile sensation of kissing while maintaining the impervious membrane to prevent the spread of germs. The handle of the frame projects a sufficient distance from the membrane so that the hand holding the frame does not interfere with contact between the kissing parties. The present invention thus helps prevent the spread of germs and viruses that can be spread from the saliva and other secretions of one person to another while kissing.

In use, the membrane is placed over the frame or holder. While grasping the handle portion of the frame or holder at a location spaced apart from the thin, flexible membrane, the user places the kissing shield under his nose, so that it covers his lips, cheeks and chin. The user then positions the kissing shield between his lips and the lips or cheek of the individual he plans to kiss and kisses the intended recipient of his affection.

In other embodiments of the present invention, the kissing shield might be a balloon shaped frame with a center web or a bag with an elongated, protrusion for use with the tongue. The device might also be sized for use as a toy by a child.

BRIEF DESCRIPTION OF THE DRAWINGS

FIG. 1 shows a plan view of the present invention with a kissing shield placed over the frame or holder and held in position for use.

FIG. 2 is a side view of the present invention shown in FIG. 1.

FIG. 4 shows a balloon shaped kissing shield having a center web with indicia to inform the user.

FIG. 5 shows a toy kissing shield.

DETAILED DESCRIPTION OF THE DRAWINGS

Figure 3:
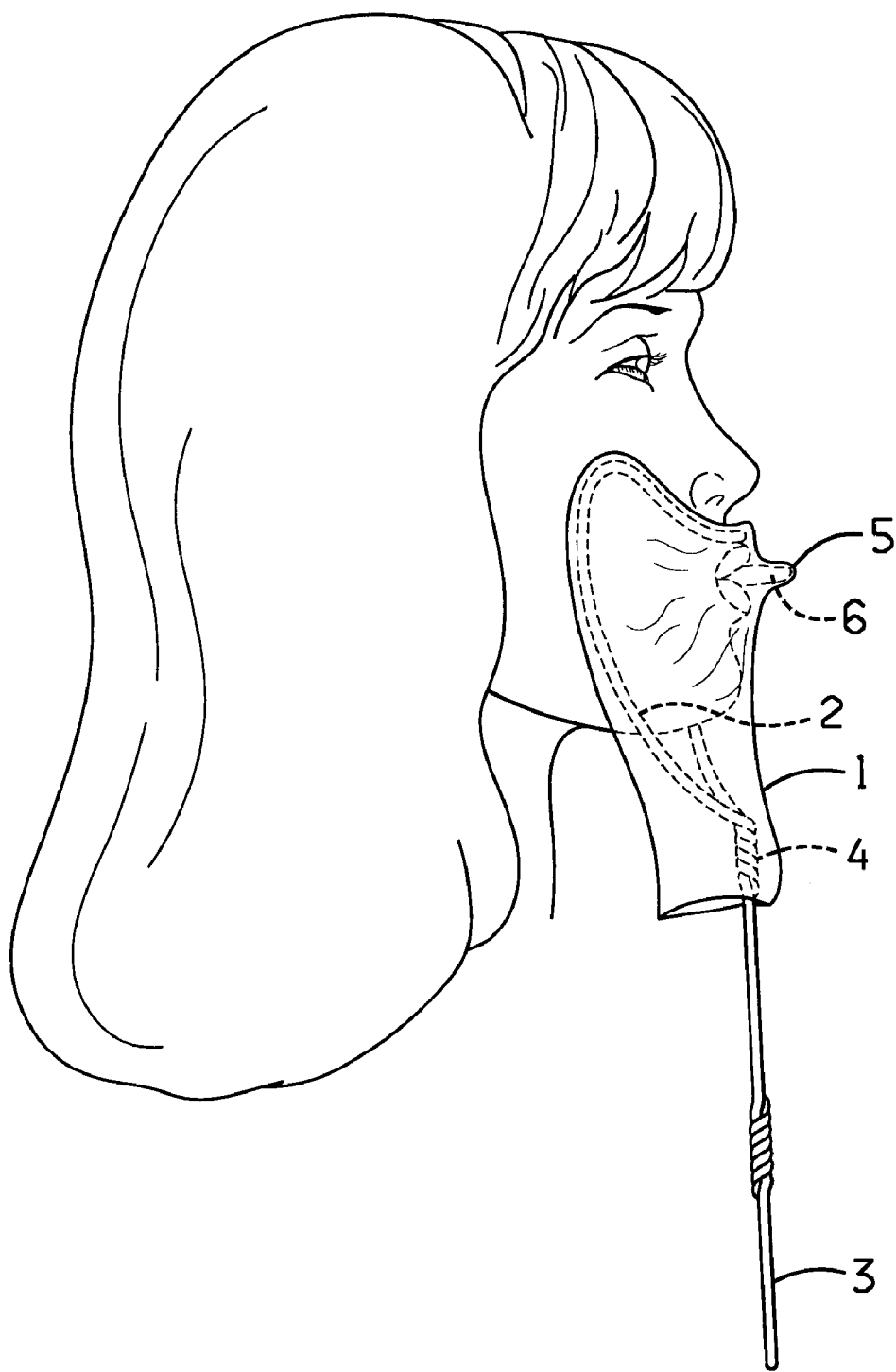
FIG. 3 is a side view of an embodiment of the present invention in which the kissing shield has a protuberance for the tongue.

Referring now to the drawings wherein like reference characters represent like elements, FIG. 1 shows a thin, flexible, impervious membrane 1 places over a holder 2 and positioned in the appropriate location for use. Membrane 1 is closed on three sides; a fourth side remains open so that the shield may be placed over frame 2. Membrane 1 may be selected from the group of thin, flexible, impervious materials, such as polyethylene, vinyl, and polypropylene. Holder 2 is comprised of a handle 3 and crook 4. Crook 4 is cordate so that it can be placed under the nose of the user while protecting the cheeks, lips, and chin of the user. Handle 3 extends laterally from crook 4 and is sized so that when the user grasps the device, his hand will be located at a distance from the membrane. It will be appreciated that membrane 1/holder 2 can be sized to be employed by a variety of users. As shown in FIG. 2, crook 4 is adapted to surround the lower part of the face of the user.

FIG. 3 shows thin, flexible, impervious membrane 1 having a protuberance 5 located near the uppermost portion of membrane 1. Protuberance 5 creates a space 6 into which the tongue of a user may be placed for a particular type of kissing.

FIG. 4 shows a balloon shaped embodiment of the present invention. In this particular embodiment, a membrane 8 is located within a donut-shaped, circular frame 7. As illustrated, a message could be located within membrane 8 for the purpose of informing the user of the proper side of the device to place against his face, among other things. It would be desirable to have the message printed in the inside of a clear membrane so as to prevent the lips from kissing the printed message.

FIG. 5 shows a flexible, plastic sheet 9 suitable for use by a child. Sheet 9 is shaped to include a handle 10, a flexure 11 to cover the cheeks of the child, and a depression 12 suitable for placement under the nose of the user. A message 13 is centered on sheet 9. Handle 10 extends laterally from flexure 11 and is sized so that when the device is used, the hand of the user will be spaced apart from flexure 11.

It should be noted that the foregoing drawings and accompanying descriptions are intended to be exemplary of several preferred embodiments of the invention and are not exhaustive of the possibilities of the types of shields within the intended scope of the invention. It should also be understood that modifications will readily occur to those skilled in the art within the spirit of the invention. Such modifications could include using different color materials on each side of the membrane or sheet to ensure that the user consistently originates his kisses from the same side of the membrane. The frame or holder onto which the thin, flexibly, impervious membrane is placed could be made of a plastic material, such as nylon, so that it could be sanitized for use by different people. The frame or holder might also be made of a firm, yet flexible material which would allow the device to be adjusted or shaped by the user for individual faces. The membrane could also be made of a plastic material which would be unaffected by products, such as foundation, lipstick, petroleum jelly, and other cosmetics routinely used by most women.

In view of the above, it will be seen that the several objects of the invention are achieved and that other advantageous results are attained. As various changes could be made in the above product and method without departing from the scope of the invention, it is intended that all matter contained in the above description or shown in the accompanying drawings shall be interpreted as illustrative and not in a limiting sense.

What is claimed is:

1. A face shield for preventing transmission of germs and the like during kissing consisting of a thin, flexible, impervious membrane mounted upon a supporting device, said device consisting of a frame portion sized to mate with said membrane and a stiff, elongated handle, said handle extending laterally from said frame portion and being sized to be grasped in the hand of the user at a point spaced apart from said frame portion.

2. A face shield according to claim 1 wherein said thin, flexible, impervious membrane consists of two sheets of thin, flexible, impervious material fastened together on three sides and open on a fourth side and the elongated handle includes a frame portion sized to pass through said fourth side of said thin, flexible, impervious membrane and to approximately mate with the interior seams of said three sides where said two sheets are fastened together.

3. A face shield according to claim 2 wherein said thin, flexibly, impervious membrane comprises a flexible bag.

4. A face shield according to claim 1 wherein said supporting device consists of said frame portion sized to support said thin, flexibly, impervious membrane and a handle portion sized so that a hand grasping said handle portion will be spaced apart from the lips of the user when the thin, flexible, impervious membrane is positioned in front of the lips of the user.

5. A face shield according to claim 1 wherein said thin, flexibly, impervious membrane further includes a protruding element in the central portion thereof, said protruding element being sized to encompass the tongue of the user.

6. A face shield according to claim 1 wherein said thin, flexible, impervious membrane is sized to cover the lips, chin, and a portion of the cheeks of the user.

7. A face shield according to claim 1 including a message or design printed in at least one surface of said thin, flexible, impervious membrane.

8. A face shield according to claim 1 wherein said thin, flexible, impervious membrane comprises a flat structure.

9. A face shield according to claim 1 wherein said thin, flexible, impervious membrane is of a synthetic material.

10. A face shield according to claim 1 wherein said thin, flexible, impervious membrane is of latex.

11. A face shield according to claim 1 wherein said thin, flexible, impervious membrane is selected from the class of polyethylene, vinyl, and polypropylene materials.

12. A face shield according to claim 1 wherein said supporting device is made of wire or plastic.

13. A face shield according to claim 1 wherein the opposite sides of said thin, flexible, impervious membrane are different in color.

14. A face shield for preventing transmission of germs and the like during kissing consisting of a supporting frame with an elongated handle projecting laterally from said frame and a pliable membrane supported on said frame.

15. A face shield according to claim 14 wherein said supporting frame is sufficiently malleable to permit it to be formed to the general contours of the face of the user, yet sufficiently rigid to support said pliable membrane.

16. A face shield according to claim 14 wherein said pliable membrane consists of a thin, flexible, impervious bag sized to easily fit over said supporting frame.

17. A face shield according to claim 14 wherein said pliable membrane is of a synthetic material.

18. A face shield according to claim 14 wherein said pliable membrane is of latex.

19. A face shield according to claim 14 wherein said pliable membrane is selected from the class of polyethylene, vinyl, and polypropylene materials.

20. A method of preventing transmission of germs and the like during kissing consisting of interposing a thin, flexible, impervious membrane in front of the lips of the kissing person, said membrane being removably mounted upon a supporting device, said supporting device consisting of a frame portion sized to mate with said membrane and a handle portion extending laterally from said frame portion, said handle portion being sized to be grasped in the hand of the user at a point spaced apart from the lips of the user when the membrane is interposed between the kissing parties, positioning the membrane proximately to the lips or check of the intended recipient of the affection, and kissing said intended recipient.

21. A method according to claim 20 wherein a separate thin, flexible membrane is removably mounted on said frame before kissing a different person.

* * * * *

UNITED STATES PATENT AND TRADEMARK OFFICE
CERTIFICATE OF CORRECTION

PATENT NO. : 6,293,280 B1
DATED : September 25, 2001
INVENTOR(S) : Deloris Gray Wood Page 1 of 1

It is certified that error appears in the above-identified patent and that said Letters Patent is hereby corrected as shown below:

Column 1,
Lines 9 through 13, delete from the word "The" to the word "abandoned".

Signed and Sealed this

Fourteenth Day of December, 2004

JON W. DUDAS
*Director of the United States Patent and Trademark Office*